US009032798B2

(12) United States Patent
Sakakibara et al.

(10) Patent No.: US 9,032,798 B2
(45) Date of Patent: May 19, 2015

(54) METHOD FOR MEASURING CRISPNESS OF FOOD PRODUCT

(75) Inventors: Michihiro Sakakibara, Fujimino (JP); Takahisa Nishizu, Gifu (JP)

(73) Assignees: NISSHIN SEIFUN GROUP INC., Tokyo (JP); GIFU UNIVERSITY, Gifu, Gifu (JP)

( * ) Notice: Subject to any disclaimer, the term of this patent is extended or adjusted under 35 U.S.C. 154(b) by 350 days.

(21) Appl. No.: 13/811,252

(22) PCT Filed: Jul. 20, 2011

(86) PCT No.: PCT/JP2011/066452
§ 371 (c)(1),
(2), (4) Date: Jan. 18, 2013

(87) PCT Pub. No.: WO2012/011494
PCT Pub. Date: Jan. 26, 2012

(65) Prior Publication Data
US 2013/0118227 A1    May 16, 2013

(30) Foreign Application Priority Data
Jul. 20, 2010    (JP) ................................ 2010-162911

(51) Int. Cl.
*G01N 19/00*    (2006.01)
*G01N 29/14*    (2006.01)
*G01N 3/40*    (2006.01)
*G01N 29/46*    (2006.01)
*G01N 33/02*    (2006.01)

(52) U.S. Cl.
CPC .................. *G01N 19/00* (2013.01); *G01N 3/40* (2013.01); *G01N 29/14* (2013.01); *G01N 29/46* (2013.01); *G01N 33/02* (2013.01); *G01N 2203/0087* (2013.01); *G01N 2291/02466* (2013.01); *G01N 2291/02827* (2013.01)

(58) Field of Classification Search
CPC ......... G01N 19/00; G01N 29/46; G01N 3/40; G01N 33/02
USPC .......................... 73/587, 12.01, 599, 600, 602
See application file for complete search history.

(56) References Cited

U.S. PATENT DOCUMENTS

| 6,792,324 | B2 * | 9/2004 | Trinkel | 700/94 |
| 2006/0262104 | A1 * | 11/2006 | Sullivan et al. | 345/177 |
| 2008/0092674 | A1 * | 4/2008 | Sakurai | 73/866.5 |
| 2011/0296964 | A1 * | 12/2011 | Muller et al. | 83/23 |

FOREIGN PATENT DOCUMENTS

| DE | 19960014 | * | 6/2001 |
| JP | 2004-12242 | A | 1/2004 |
| JP | 3567199 | | 9/2004 |
| JP | 2004-294173 | A | 10/2004 |
| JP | 2005-147804 | A | 6/2005 |
| JP | 2006-227021 | A | 8/2006 |
| JP | 2007-57476 | A | 3/2007 |

* cited by examiner

*Primary Examiner* — J M Saint Surin
(74) *Attorney, Agent, or Firm* — Muncy, Geissler, Olds & Lowe, P.C.

(57) ABSTRACT

Provided are a device (10) and a method for measuring the crispness of a food product. An item to be measured (22) comprising a porous food product is broken apart by causing the blade of a knife (14) to penetrate into the item. A vibration detector (18) attached to the knife (14) detects crack vibrations from cracks that form when the item to be measured (22) is broken apart. In a computer (20), the small crack vibrations of a predetermined vibration power or less that are included in the crack vibrations within an individual cracking duration time are extracted from the detected crack vibrations. Crispness is measured on the basis of the number of extracted small crack vibrations counted (number of cracks).

8 Claims, 7 Drawing Sheets

METHOD FOR MEASURING CRISPNESS OF FOOD PRODUCT

TECHNICAL FIELD

The present invention relates to a device and a method for measuring the crispness of a food product with which measurement is made for evaluating the crispness as an important texture of porous food products including deep-fried food products.

BACKGROUND ART

A microphone has been conventionally used to make measurement in the method of measuring the crispness (so-called crispy texture) of deep-fried food products such as tempura (Japanese fritter-like dish) and korokke (a kind of croquette). However, there are differences in the perception of the crispness among individuals and its evaluation was subjective. What is more, the sensory factor which may cause people to perceive crispness has been less studied.

Under the circumstances, Patent Literature 1 discloses a method of evaluating the texture of a porous food product, the method comprising: subjecting sound and/or vibrations occurring during the breakage and/or mastication of a porous food product such as a deep-fried food product to acoustic analysis using the sharpness and/or roughness as the amount for acoustic evaluation, and using the numerical values obtained by the acoustic analysis to evaluate the crispness of the porous food product without evaluation through the sensory test.

Patent Literature 2 discloses a device for measuring the physical properties of a food product, wherein the texture value of the food product is obtained by inserting a thrust jig having projections and recesses formed on lateral faces thereof, into a sample such as the food product, detecting vibrations occurring during the insertion, performing Fourier transform to convert the vibrations into a vibration spectrum, and carrying out an operation of the vibration spectrum and a coefficient table.

CITATION LIST

Patent Literature

Patent Literature 1: JP 2006-227021 A
Patent Literature 2: JP 3567199 B

SUMMARY OF INVENTION

Technical Problems

However, in the method of evaluating the texture of a porous food product as described in Patent Literature 1 and the device for measuring the physical properties of a food product as described in Patent Literature 2, continuous sound or vibrations occurring during the breakage, mastication and penetration are all used to perform data analysis and therefore it was difficult to detect at a high sensitivity differences of the crispness which is important to evaluate a deep-fried food product or the like, and correct measurement of the crispness and hence correct evaluation of a deep-fried food product or the like could not be performed.

Continuous sound or vibrations occurring during the breakage and mastication of a measurement target such as a deep-fried food product, and the penetration thereinto, that is, tissue-breakdown vibrations (hereinafter referred to as "crack vibrations") of the measurement target are vibrations based on cracks upon breakage of batter of the deep-fried food product and such vibrations occur based on a variety of cracks including from large cracks to very small cracks.

In order to solve the above-described problems, the invention aims at providing a device and a method for measuring the crispness of a food product, the device and the method being capable of detecting differences of the crispness at a high sensitivity using information on crack vibrations such as continuous sound or vibrations occurring during the breakage and mastication of a porous food product such as a deep-fried food product and the penetration thereinto, and of correctly evaluating the crispness which is an important index for the correct evaluation of a porous food product such as a deep-fried food product.

Solution to Problems

In order to solve the prior art problems and achieve the foregoing object, the inventors of the invention focused their attention on the sound or vibrations resulting from comparatively small breakdown of batter of a deep-fried food product, that is, comparatively small tissue-breakdown vibrations (hereinafter referred to as "small crack vibrations"). No attention has conventionally been drawn to the small crack vibrations because the small crack vibrations were masked by the sound or vibrations resulting from large breakdown of a deep-dried food product when measurement was made for all the crack vibrations which are continuous sound or vibrations based on the cracks during the breakage of batter of the deep-fried food product and occurring during the breakage and mastication of the food product and the penetration thereinto.

The inventors of the invention subjected all of these crack vibrations to spectral analysis using the maximum entropy method and focused their attention on the level peak of the resulting power spectra and as a result found that the number of small crack vibrations showing the power at a lower level in all the spectra, that is, the number of cracks (i.e., the number of small cracks) tends to decrease over time and that the number of small cracks is effective as an index of crispness.

In other words, the inventors of the invention found that the small crack vibrations correctly represent the crispness and the differences in crispness can be correctly evaluated by the differences in the small crack vibrations and, by separating the small crack vibrations from all the crack vibrations, detecting the separated small crack vibrations and using information on the detected small crack vibrations, the differences in crispness of a porous food product such as a deep-fried food product can be detected at a high sensitivity to enable correct measurement of the crispness and as a result correct evaluation of the porous food product such as the deep-fried food product.

In order to achieve the foregoing object, a first aspect of the invention provides a device for measuring crispness of a food product, comprising: breaking means including an edge and breaking a measurement target comprising a porous food product by causing the edge to penetrate the measurement target; a vibration detector being in close contact with the breaking means and detecting crack vibrations comprising sound and/or vibrations based on cracks occurring in the measurement target upon breakage of the measurement target with the edge of the breaking means; small crack extracting means extracting small crack vibrations having vibration power not larger than specified vibration power included in crack vibrations within each individual crack duration from the crack vibrations detected by the vibration detector; and measurement means counting, as small cracks, the small crack vibrations within the each individual crack duration extracted by the small crack extracting means and measuring crispness based on a number of counted small cracks, namely, the number of cracks.

The small crack extracting means preferably extracts as the small crack vibrations crack vibrations having peak power which is up to 10%, preferably up to 5% and most preferably up to 1% on a maximum value of the peak power in a power spectrum of the crack vibrations within the each individual crack duration (maximum peak power value in the whole group of measurement targets to be compared).

The small crack extracting means preferably cuts the crack vibrations for the each individual crack duration from the crack vibrations to perform filtering on them and performs spectral analysis on them using a maximum entropy method to determine the power spectrum.

The vibration detector is preferably a contact microphone or a piezoelectric device.

Preferably, the breaking means is a knife, the crispness measuring device of the invention further comprises a stage vertically moving at a constant speed and a wedge-shaped pressing member pressing a back side of the knife, or a stage and a wedge-shaped pressing member vertically moving at a constant speed and pressing the back side of the knife, the measurement target is put on the stage so that the knife comes into vertical contact with the measurement target and the knife comes into point contact with a wedge portion of the wedge-shaped pressing member, and the stage moves upward at a constant speed or the wedge-shaped pressing member moves downward at a constant speed to cause the measurement target to be broken by the knife.

In order to achieve the foregoing object, a second aspect of the invention provides a method for measuring crispness of a food product, comprising: a breaking step for breaking a measurement target comprising a porous food product by causing an edge to penetrate the measurement target; a detecting step for detecting crack vibrations comprising sound and/or vibrations based on cracks occurring in the measurement target upon breakage of the measurement target with the edge in the breaking step; an extracting step for extracting small crack vibrations having vibration power not larger than specified vibration power included in crack vibrations within each individual crack duration from the crack vibrations detected in the detecting step; and a measuring step for counting, as small cracks, the small crack vibrations within the each individual crack duration extracted in the extracting step and measuring crispness based on a number of counted small cracks, namely, the number of cracks.

The extracting step preferably extracts as the small crack vibrations crack vibrations having peak power which is up to 10%, preferably up to 5% and most preferably up to 1% on a maximum value of the peak power in a power spectrum of the crack vibrations within the each individual crack duration.

The extracting step preferably cuts the first crack vibrations for the each individual crack duration from the crack vibrations to perform filtering on them and performs on them spectral analysis on them using a maximum entropy method to determine the power spectrum.

Advantageous Effects of Invention

The invention can provide a device and a method for measuring the crispness of a food product which are capable of detecting the differences in crispness at a high sensitivity and of correctly evaluating the crispness as an important index for the correct evaluation of a porous food product such as a deep-fried food product by improving the detection sensitivity of small crack vibrations which have been difficult to detect with a conventional measurement method and were found by the inventors to be effective as the index of the crispness, and by making efficient use of information on the small crack vibrations masked by the large crack vibrations in conventional data analysis.

DESCRIPTION OF EMBODIMENTS

The device and method for measuring the crispness of a food product according to the invention are described below in detail based on preferred embodiments shown in the accompanying drawings.

Preferable examples of the food product of which the crispness can be evaluated by the device and method for measuring the food product's crispness according to the invention include porous food products each having a porous tissue structure. Exemplary porous food products include deep-fried food products such as tempura, kakiage (tempura made with mixed seafoods and/or vegetable strips), deep-fried breaded fish and vegetables, katsuretsu (breaded and fried cutlet), and batter used therefore; confectionery such as cookies, biscuits, crackers and cereals; rice confectionery such as senbei (Japanese rice cracker) and arare (bit-sized Japanese rice cracker); and puffed food products such as puffed cereals. Of those, deep-fried food products are preferable and tempura is most preferable.

Figure 1:
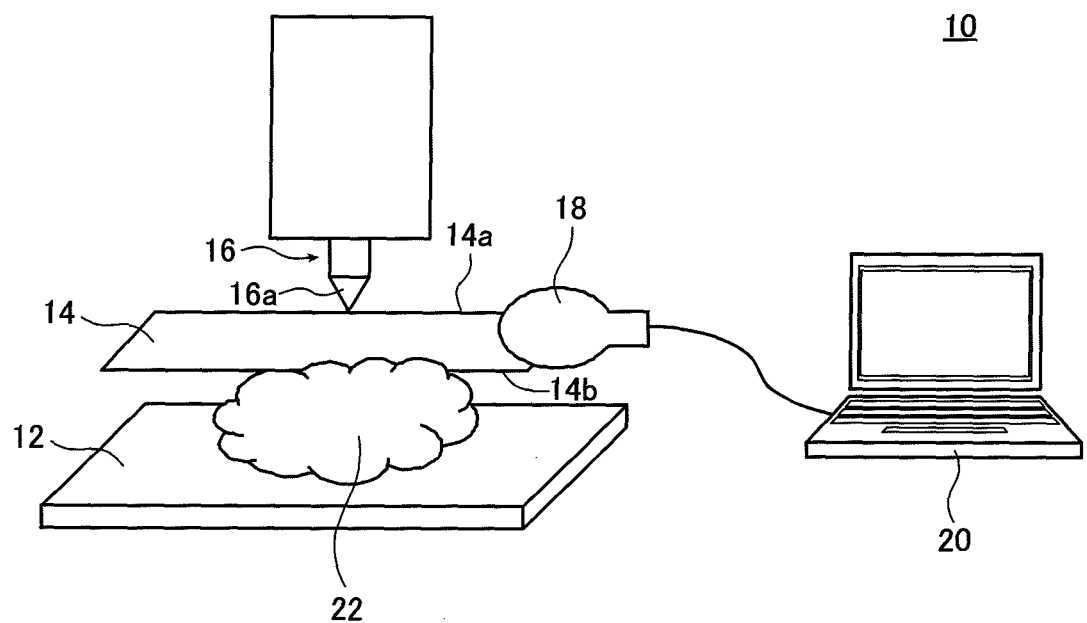
FIG. 1 is a schematic configuration diagram of an embodiment illustrating the configuration of a device for measuring the crispness of a food product according to the invention.

FIG. 1 is a schematic configuration diagram of an embodiment illustrating the configuration of a device 10 for measuring the crispness of a food product according to the invention with which the crispness measuring method of the invention is implemented.

The crispness measuring device 10 shown in FIG. 1 includes a stage 12, a knife 14, a wedge-shaped pressing member 16, a contact microphone 18 and a computer 20.

The stage 12 is used to put a measurement target 22 including a porous food product, for example, a deep-fried food product such as tempura, and a stage of a device in which the stage or a plunger moves at a constant speed as in, for example, a texture analyzer or a rheometer may be used. The vertical movement of the stage 12 at a constant speed causes the measurement target 22 to be broken by the knife 14 to be described later. It is also possible to fix the stage 12 and to move the knife 14 and the wedge-shaped pressing member 16 vertically at a constant speed.

The knife 14 is a breaking means and is a metal knife which is longer than the measurement target 22 and has an edge, that is, a knife edge 14b on its one side along the longitudinal direction. At the initial state before the start of the measurement, the knife 14 is disposed so that the knife edge 14b may come into contact with the measurement target 22 on its upper side, for example, come into contact therewith vertically. The knife 14 used may have edges on both sides thereof.

The wedge-shaped pressing member 16 is in contact with a back side 14a of the knife 14 and when the stage 12 is moved upward, causes the knife edge 14b of the knife 14 to be pressed into the measurement target 22, for example vertically. A wedge portion 16a of the wedge-shaped pressing member 16 is disposed so as to be, for example, vertical to the back side 14a of the knife 14.

The contact microphone 18 functions as a vibration detector in the invention. It is disposed in close contact with one end of the knife 14 and detects crack vibrations occurring as a result of the breakage of the measurement target 22 caused by the knife 14. The contact microphone 18 may be replaced by a piezoelectric device.

When the detection is made using a conventional microphone, the vibration energy generated by the breakage of the measurement target 22 propagates as sound in the air having an extremely small acoustic impedance compared to the measurement target 22 and therefore the energy loss was large and the sound derived from small cracks (small crack vibrations) was difficult to detect.

In contrast, the contact microphone 18 is in close contact with the knife 14 which is made of metal and has a larger acoustic impedance than air, and the knife 14 is in contact with the fracture surface of the measurement target 22. Therefore, the sensitivity for detection of small crack vibrations is improved.

In cases where a common texture analyzer or rheometer is used, vibrations are attenuated at the plunger portion and the rod portion and the response frequency of a load cell is at most a few kHz, and therefore the sensitivity for high-frequency detection is reduced.

Figure 2:
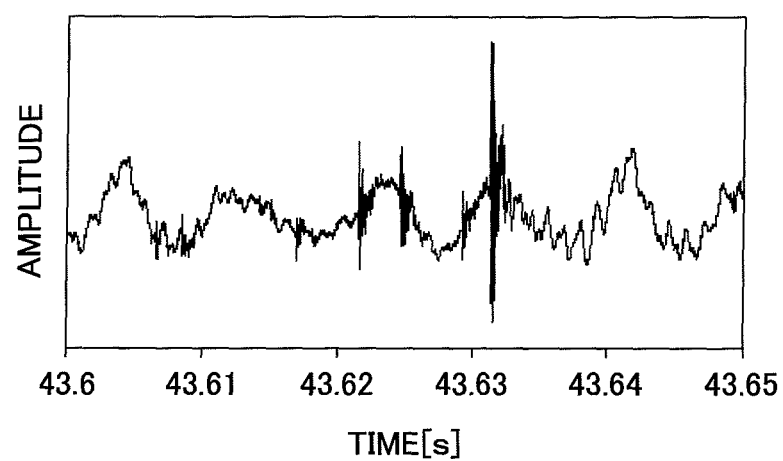
FIG. 2 is a graph showing the original waveform of crack vibrations.

The computer 20 is one with sound recording capability. The computer 20 functions as a small crack extracting means and a crispness detecting means in this invention. The computer 20 cuts individually independent crack vibrations after threshold processing out of, for example, the crack vibrations as shown in FIG. 2 having been detected by the contact microphone 18, subjects the crack vibrations to data analysis, extracts small crack vibrations having vibration power not larger than specified vibration power which are included in crack vibrations within each individual crack duration, counts the small crack vibrations extracted within each individual crack duration to obtain the frequency of the counted small crack vibrations (number of counts) as the number of cracks, and evaluates and measures the crispness based on the resulting number of cracks, in other words, based on the number of small cracks obtained by counting the small crack vibrations as the small cracks. The crack duration as used herein refers to a time period over which crack detection is possible from the start of contact of the knife 14 with the measurement target to the stop of the knife 14.

Figure 3:
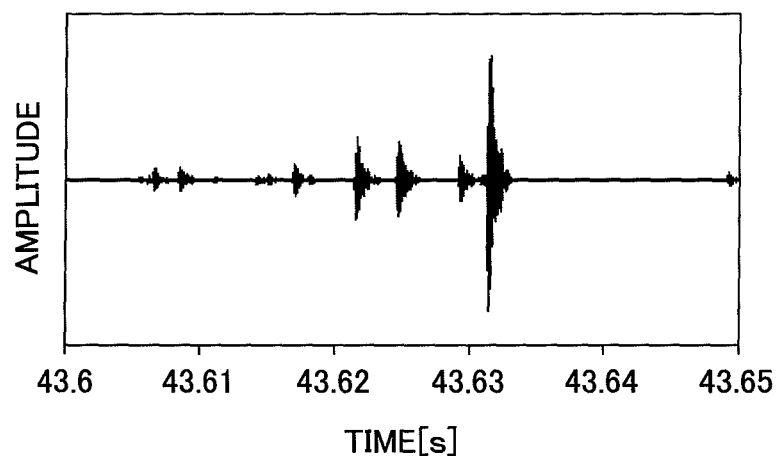
FIG. 3 is a graph showing the waveform of the crack vibrations after filtering.

The computer 20 preferably performs filtering, such as low-frequency trend elimination with a Savitzky-Golay filter, on the crack vibrations as shown in FIG. 2, for example. The waveform after the filtering is shown in FIG. 3. In addition, the filtering is preferably followed by spectral analysis using the maximum entropy method (MEM) to determine the power spectrum.

Instead of having the sound recording capability, the computer 20 may be configured so that data recorded by a sound recorder (not shown) is inputted to the computer 20 by connecting the sound recorder to the computer 20 and the microphone 18 to the sound recorder.

According to the invention, in the data analysis, the low-frequency trend elimination using the foregoing filter is performed to detect each crack vibration constituting the vibrations occurring in the breaking step and subsequently the spectral analysis is performed by the maximum entropy method to calculate the vibration energy of each crack vibration, which makes it possible to use all of the small crack vibrations in the data analysis.

The small crack vibrations can be extracted, for example, as crack vibrations having peak power which is up to 10%, preferably up to 5% and most preferably up to 1% on the maximum value of the peak power in the power spectrum of the crack vibrations within each individual crack duration.

In the invention, the small crack vibrations are deemed as the crack vibrations having peak power which is up to 10% on the maximum value of the peak power in the power spectrum of the crack vibrations within each individual crack duration. This is because at a value exceeding 10%, the ratio of large tissue-breakdown vibrations which are perceived not as crispy but as raspy or crunchy is increased to considerably reduce the correlation between the number of cracks and the crispness.

The small crack vibrations are most preferably extracted as the crack vibrations which are each 1% or less in peak power on the maximum value because the ratio of large tissue-breakdown vibrations which are perceived as raspy or crunchy is reduced to almost zero to increase the correlation between the number of cracks and the crispness.

Next, the operation of the crispness measuring device of the invention and the crispness measuring method of the invention are described with reference to FIGS. 1 and 11.

Figure 11:
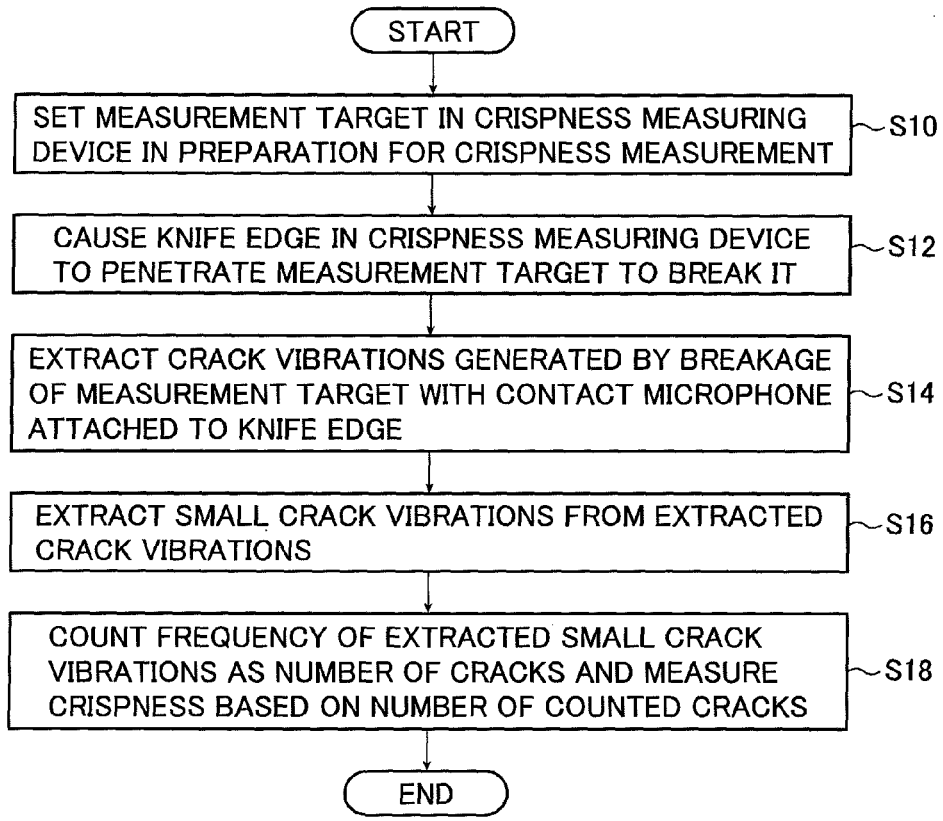
FIG. 11 is a flowchart illustrating an embodiment of a method for measuring the crispness of a food product according to the invention.

FIG. 11 is a flowchart illustrating an embodiment of the method for measuring the crispness of a food product according to the invention.

First of all, in Step S10, in preparation for the measurement of the crispness of a porous food product such as tempura using the crispness measuring device 10 shown in FIG. 1, the porous food product is put on the stage 12 as the measurement target 22 and adjusted so that the knife edge 14b of the knife 14 with which the contact microphone 18 is in close contact may come into vertical contact with the measurement target 22 and the back side 14a of the knife 14 may come into point contact with the wedge portion 16a of the wedge-shaped pressing member 16. Thus, the measurement target 22 is set in the crispness measuring device 10 and the preparation for the crispness measurement of the measurement target 22 is completed.

Then, the crispness measurement is started.

In Step S12, the stage 12 is raised at a constant speed to cause the edge of the knife 14 to penetrate the measurement target 22, thus breaking the measurement target 22.

At the same time, in Step S14, crack vibrations including sound and/or vibrations based on cracks generated in the measurement target 22 as a result of the breakage of the measurement target 22 caused by the edge of the knife 14 are detected by the contact microphone 18 which is in close contact with the knife 14. The signals of the detected crack vibrations are recorded in the computer 20.

Subsequently, in Step S16, small crack vibrations having vibration power not larger than specified vibration power which are included in the crack vibrations within each individual crack duration are extracted in the computer 20 from the crack vibrations detected in Step S14.

In Step S16, it is preferable to first cut out the crack vibrations detected in Step S14 for each individual crack duration and perform filtering to eliminate low-frequency components thereby obtaining signals for only high-frequency cracks, and process these signals according to the maximum entropy method (MEM) to extract the cracks in the signal waveform one by one and subject the extracted cracks to spectral analysis to determine the power spectrum.

In Step S16, it is preferable to extract, as the small crack vibrations, the crack vibrations having peak power which is up to 10%, more preferably up to 5% and most preferably up to 1% on the maximum value of the peak power in the power spectrum of the crack vibrations within each individual crack duration.

Next, in Step S18, the small crack vibrations within each individual crack duration as extracted in Step S16 are counted as small cracks and the crispness is measured based on the frequency of the counted small cracks (number of cracks). More specifically, the crispness can be measured by using the number of the counted cracks as the index for evaluating the crispness.

The crispness of the porous food product such as tempura can be thus measured.

EXAMPLES

Next, the operation of the crispness measuring device of the invention and the crispness measuring method of the invention are described more specifically by way of specific examples of the above-described embodiment.

The raw materials of the measurement target (hereinafter also referred to as the "sample") used in Examples were Sasa-kamaboko (a bamboo-leaf-shaped fish cake made from whitefish, sake and salt), tempura flour and salad oil. A household deep fryer (DF380 manufactured by De'Longhi) was used for deep frying and a radiation thermometer (IT-340 manufactured by HORIBA, Ltd.) was used to check the oil temperature.

According to the optimal preparation conditions of the tempura flour, 200 g of ice water was added to 100 g of flour and the mixture was stirred with a whisk for 1 minute to prepare batter. The Sasa-kamaboko cut into half pieces was dipped in the batter and the samples were deep-fried one by one in the salad oil heated to about 180° C. for 1 minute and 30 seconds. The samples taken out of the oil were put on tempura paper and allowed to stand at room temperature for a given length of time (0 to 25 minutes) before using in the measurement of the crack sound.

In Examples, the samples deep-fried by the above-described method were used for the measurement target 22 and the crispness measuring device used was the crispness measuring device 10 shown in FIG. 1.

The deep-fried food product such as tempura was put as the measurement target 22 on the stage 12 of the crispness measuring device 10 shown in FIG. 1 and the stage was vertically moved while supporting the knife 14, thereby making adjustments so that the knife edge 14b of the knife 14 with which the contact microphone 18 was in close contact could come into vertical contact with the measurement target 22 and the back side 14a of the knife 14 could come into point contact with the wedge portion 16a of the wedge-shaped pressing member 16. In other words, the knife 14 was fixed by the measurement target 22 and the wedge-shaped pressing member 16 so as to be sandwiched therebetween from the upper and lower directions. As compared to the case where people eat a deep-fried food product such as tempura to evaluate the texture, the stage 12, the wedge-shaped pressing member 16, the knife 14 and the contact microphone 18 may play the roles of the lower jaw, upper jaw, teeth and ears, respectively.

Next, the measurement was started. The stage 12 was raised at a constant speed to break (or cut; this action corresponds to mastication) the measurement target 22 with the edge of the knife 14. Crack sound (crack vibrations) during the breakage was detected by the contact microphone 18 which was in close contact with the knife 14 and the output from the contact microphone 18 was recorded in the computer 20. The ascent rate of the stage 12 (i.e., cutting rate) was set to 100 mm/min and the elevation distance (amount of cutting) to 6 mm.

In order to eliminate the vibrations of the movable stage 12 and the low-frequency trends from the original waveform of the signals outputted from the contact microphone 18 and recorded in the computer 20, the data analysis software Origin 8 (Lightstone Corp.) was used to eliminate high-frequency crack signals through a Savitzky-Golay filter (quadratic, 21 points on one side) and subtract the filtered waveform from the original waveform to thereby obtain signals only for the high-frequency cracks.

Subsequently, the 50th order maximum entropy method (MEM) was performed to extract the cracks in the waveform one by one and subject the extracted cracks to spectral analysis. Spectral energy at 20 kHz or less was calculated from the power spectrum obtained by the spectral analysis and the duration of the cracks, and four elements were calculated for each crack, the number of points (A) at the time when the relevant crack appeared, the duration (B) of the relevant crack, the spectral peak power (C) and the vibration power (D). The spectral energy at 20 kHz or less represents that, when data acquired at a sampling rate of 44.1 kHz is used, spectra at 22.05 kHz or less can be acquired according to the sampling theorem and generally all the spectral energy is calculated.

Next, the peak power of each power spectrum analyzed for all the crack vibrations was divided by the maximum value of the peak power and thus normalized, the crack vibrations having peak power of 0.01 (1%) or less were extracted as small crack vibrations and the number thereof was counted as the crack frequency (number of cracks).

Figure 4:
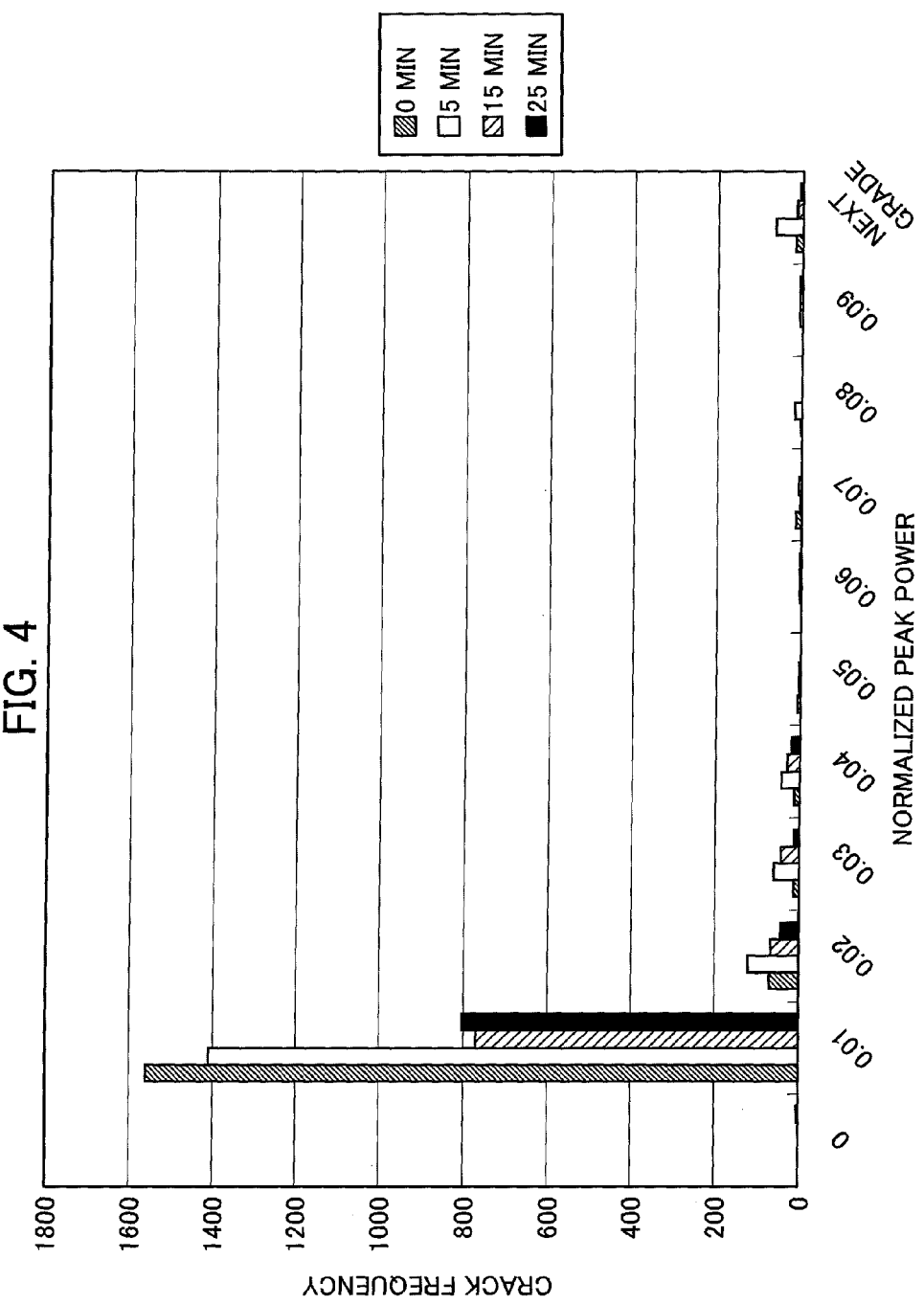
FIG. 4 is a graph of temporal comparison results of the frequency distribution of the normalized peak power.

A graph of the temporal comparison results of the power level frequency distribution is shown in FIG. 4. In FIG. 4, the horizontal axis shows the peak power of the analyzed power spectra normalized through division by the peak maximum value, and the vertical axis shows the crack frequency (number of cracks) in each grade just after deep frying (0 minutes), after the lapse of 5 minutes, after the lapse of 15 minutes, and after the lapse of 25 minutes.

FIG. 4 shows that, of all the cracks, the ratio of small cracks with normalized peak power of 0.01 or less is very large and that the number of the small cracks tends to decrease over time. That is, it is revealed that the number of the small cracks considerably contributes toward the changes over time of the total number of cracks.

Next, the values of (A) to (D) in the small cracks having normalized peak power (D) of 0.01 or less were used to calculate the number of cracks per second (E), the vibration power per second (F), the average peak power (G) of power spectra and the total vibration energy (H) of all the cracks according to the following formulae (1) to (4):

$$(E) = \text{total number of small cracks with } (D) \text{ of less than } 0.01/\text{cutting time (second)} \quad (1)$$

$$(F) = \text{sum of } (D) \text{ of all the small cracks/cutting time (second)} \quad (2)$$

$$(G) = \text{average of } (C) \text{ of all the small cracks} \quad (3)$$

$$(H) = \text{vibration power } (F) \text{ of each small crack} \times \text{sum of crack durations } (B)$$

Figure 5:
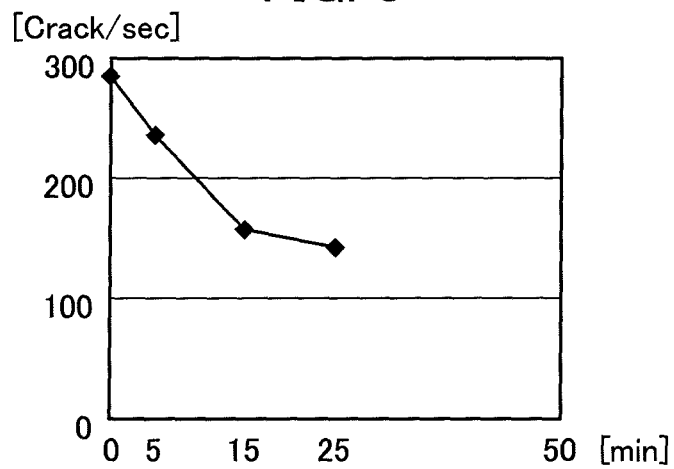
FIG. 5 is a graph showing the number of small cracks per second.
Figure 6:
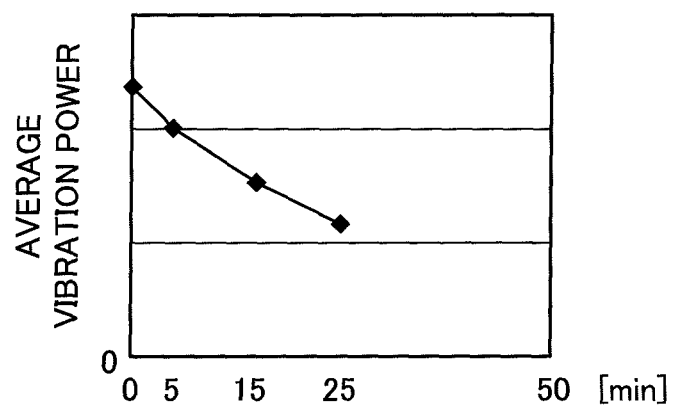
FIG. 6 is a graph showing the vibration strength (vibration power) per second generated by the small cracks.
Figure 7:
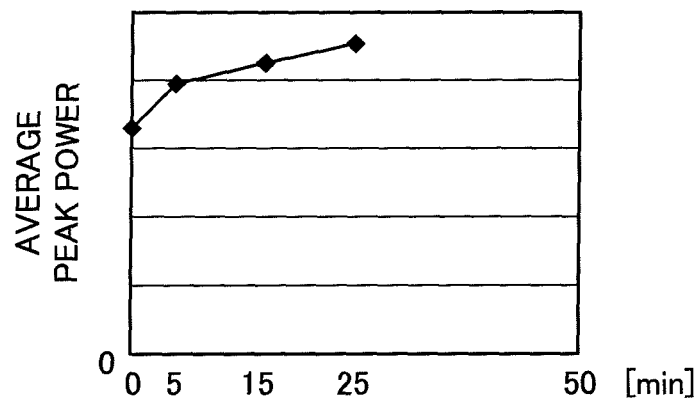
FIG. 7 is a graph showing the average peak power of the small cracks.
Figure 8:
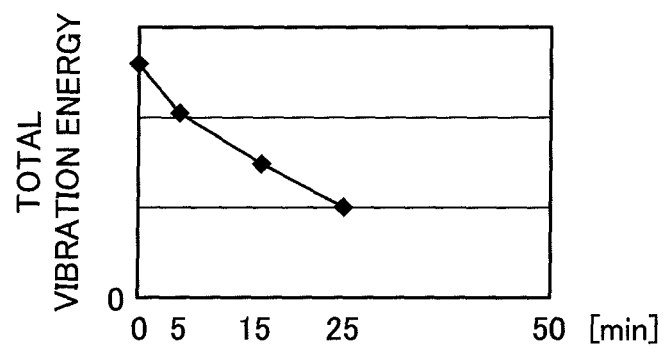
FIG. 8 is a graph showing the total vibration energy from the small cracks.
Figure 9:
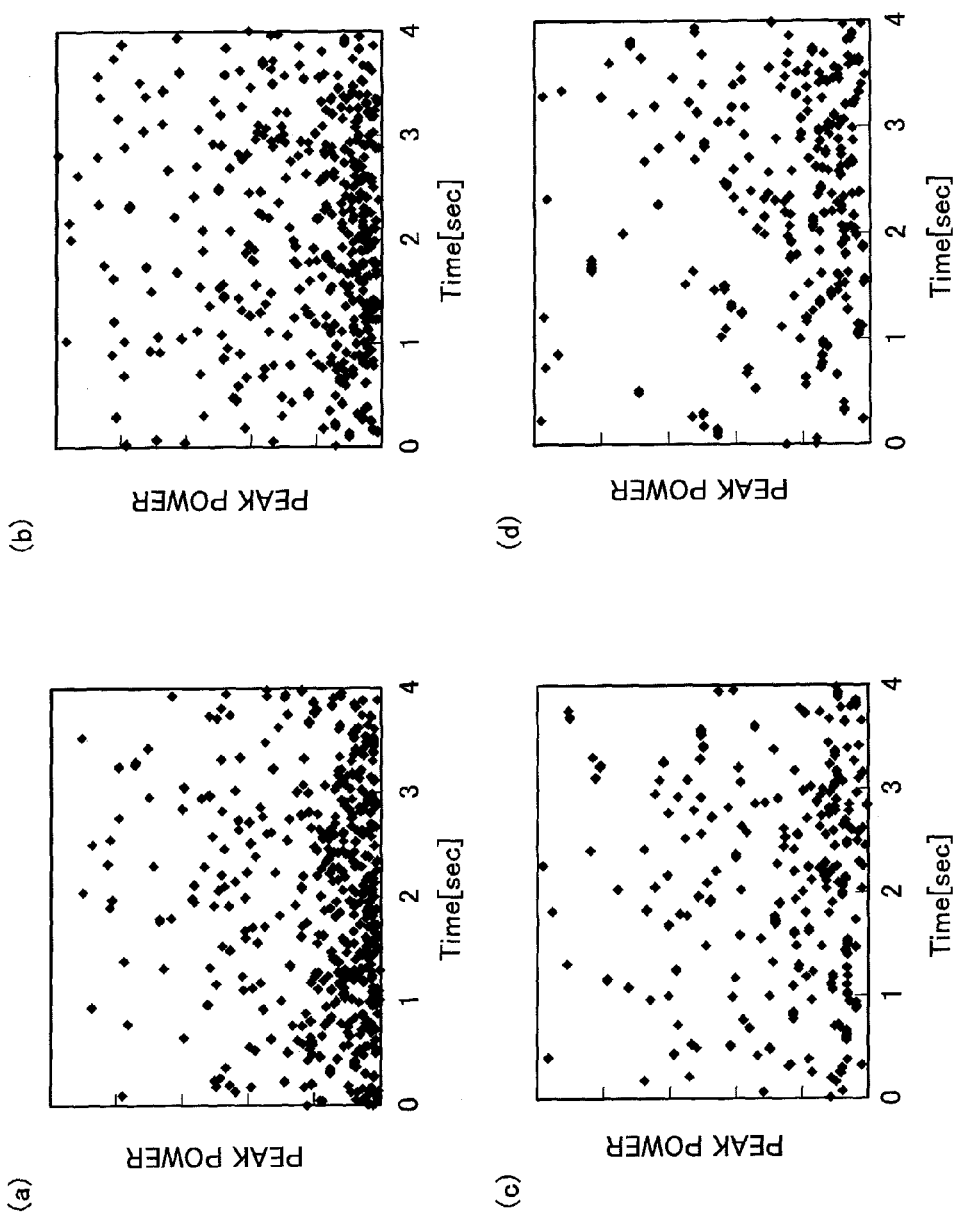
FIG. 9($a$) to FIG. 9($d$) each show a graph of the distribution of small cracks with normalized peak power of less than 0.01.
Figure 10:
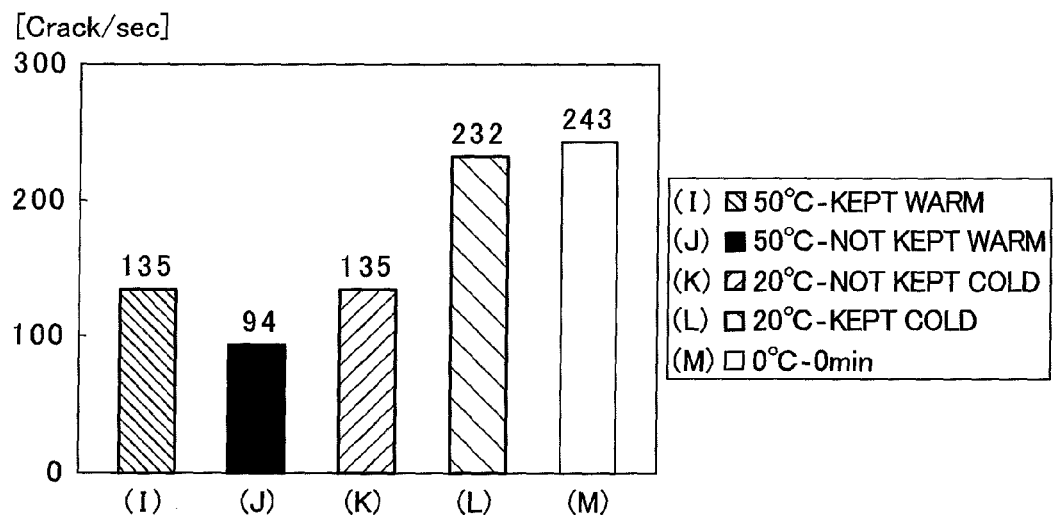
FIG. 10 is a graph showing the number of small cracks in samples using batter with different crispness.

FIG. 5 shows the number of small cracks per second (E), FIG. 6 the vibration power per second (F) generated by the cracks, FIG. 7 the average peak power (G), and FIG. 8 the total vibration energy (H) generated by the cracks.

The number of small cracks per second (E) shown in FIG. 5 is obtained by dividing the numbers of cracks with normalized peak power of 0.01 or less after the lapse of 0 minutes, 5 minutes, 15 minutes and 25 minutes in FIG. 4 by the cutting times of the four cases, respectively. FIG. 5 shows that the number of small cracks per second tends to decrease over time, and the vibration power per second as shown in FIG. 6 and the total vibration energy as shown in FIG. 8 also tend to decrease. In contrast, it is revealed that only the average peak power as shown in FIG. 7 increases over time.

The increase over time of the average peak power as shown in FIG. 7 is described.

The distributions of the small cracks with peak power of 0.01 or less in the measurement target 22 (sample) just after deep frying (0 minutes), after the lapse of 5 minutes, after the lapse of 15 minutes and after the lapse of 25 minutes have been shown in FIG. 9(a) to FIG. 9(d). FIG. 9(a), FIG. 9(b), FIG. 9(c) and FIG. 9(d) show the states just after deep frying (0 minutes), after the lapse of 5 minutes, after the lapse of 15 minutes, and after the lapse of 25 minutes, respectively.

It is revealed from FIG. 9(a) to FIG. 9(d) that the distribution of the small cracks decreases over time after deep frying and of those, cracks with less vibration power decrease considerably. The small cracks with less vibration power decrease and therefore based on the average peak power of all the small cracks, it is revealed that the average peak power as shown in FIG. 7 increases over time.

From the above, it is also revealed that, of those crack vibrations, the small crack vibrations having peak power which is up to 0.01 (1%) on the maximum value serve as an excellent index for evaluating the crispness and that the number of the small cracks is excellent as an index for evaluating the crispness.

REFERENCE EXAMPLE

Reference Example shows an example of commonly used sensory crispness evaluation.

The measurement target used was the same as that used in the above-described Examples and 10 panelists evaluated it according to the evaluation criteria shown in Table 1. The evaluation results are shown in Table 2.

TABLE 1

| Rating | Evaluation criteria |
| --- | --- |
| 5 | Very crispy and very light in texture |
| 4 | Crispy and light in texture |
| 3 | Slightly crispy |
| 2 | Slightly chewy |
| 1 | Feel very chewy |

TABLE 2

| | Score |
| --- | --- |
| Just after deep frying (0 min) | 5 |
| 5 minutes after deep frying | 4.5 |
| 15 minutes after deep frying | 4.1 |
| 25 minutes after deep frying | 3.9 |

The decreasing trend of the number of small cracks as shown in FIG. 5 and the decreasing trend of the score in the sensory evaluation results as shown in Table 2 show the same decreasing trend, which reveals that the crispness can be quantitatively measured by determining the number of small cracks and be evaluated objectively.

The device and method for measuring the crispness of a food product according to the invention may also be used not only in the measurement of the crispness of a deep-fried food product but also in the measurement of the crispness of crispy food products including a porous food product and a foam-containing food product.

While the device and method for measuring the crispness of a food product according to the invention have been described above in detail, the invention is by no means limited to the foregoing embodiments and it should be understood that various improvements and modifications are possible without departing from the scope and spirit of the invention.

INDUSTRIAL APPLICABILITY

The device and method for measuring the crispness of a food product according to the invention separate, from all the crack vibrations, small crack vibrations that have been masked by large crack vibrations in conventional data analysis, detect the separated small crack vibrations, and make efficient use of information on the detected small crack vibrations, and are therefore useful in the correct crispness measurement and as a result are extremely useful in the correct evaluation of a porous food product such as a deep-fried food product.

DESCRIPTION OF SYMBOLS 10, 50 crispness measuring device
12 stage
14 knife
14a back side
14b knife edge
16 wedge-shaped pressing member
16a wedge portion
18 contact microphone
20 computer
22 measurement target (sample)

The invention claimed is:
1. A crispness measuring device comprising:
breaking means including an edge and breaking a measurement target comprising a porous food product by causing said edge to penetrate said measurement target;
a vibration detector being in close contact with said breaking means and detecting crack vibrations comprising sound and/or vibrations based on cracks occurring in said measurement target upon breakage of said measurement target with said edge of said breaking means;

small crack extracting means extracting small crack vibrations having vibration power not larger than specified vibration power included in first crack vibrations within each individual crack duration from said crack vibrations detected by said vibration detector; and measurement means counting said small crack vibrations within said each individual crack duration extracted by said small crack extracting means and measuring crispness based on a number of counted cracks.

2. The crispness measuring device according to claim 1, wherein said small crack extracting means extracts as said small crack vibrations crack vibrations having peak power which is up to 10% on a maximum value of peak power in a power spectrum of said first crack vibrations within said each individual crack duration.

3. The crispness measuring device according to claim 2, wherein said small crack extracting means cuts said first crack vibrations for said each individual crack duration from said crack vibrations to perform filtering on said cut first crack vibrations and performs on said first crack vibrations performed filtering spectral analysis using a maximum entropy method to determine said power spectrum.

4. The crispness measuring device according to claim 1, wherein said vibration detector is a contact microphone or a piezoelectric device.

5. The crispness measuring device according to claim 1, wherein said breaking means is a knife, wherein said crispness measuring device further comprises a stage vertically moving at a constant speed and a wedge-shaped pressing member pressing a back side of said knife, or a stage and a wedge-shaped pressing member vertically moving at a constant speed and pressing the back side of said knife, wherein said measurement target is put on said stage so that said knife comes into vertical contact with said measurement target and said knife comes into point contact with a wedge portion of said wedge-shaped pressing member, and wherein said stage moves upward at a constant speed or said wedge-shaped pressing member moves downward at a constant speed to cause said measurement target to be broken by said knife.

6. A crispness measuring method comprising the steps of:

a breaking step of breaking a measurement target comprising a porous food product by causing an edge to penetrate said measurement target;

a detecting step of detecting crack vibrations comprising sound and/or vibrations based on cracks occurring in said measurement target upon breakage of said measurement target with said edge in said breaking step;

an extracting step of extracting small crack vibrations having vibration power not larger than specified vibration power included in first crack vibrations within each individual crack duration from said crack vibrations detected in said detecting step; and a measuring step of counting said small crack vibrations within said each individual crack duration extracted in said extracting step and measuring crispness based on a number of counted cracks.

7. The crispness measuring method according to claim 6, wherein said extracting step extracts as said small crack vibrations crack vibrations having peak power which is up to 10% on a maximum value of peak power in a power spectrum of said first crack vibrations within said each individual crack duration.

8. The crispness measuring method according to claim 7, wherein said extracting step cuts said first crack vibrations for said each individual crack duration from said crack vibrations to perform filtering on said cut first crack vibrations and performs on said first crack vibrations performed filtering spectral analysis using a maximum entropy method to determine said power spectrum.

* * * * *